United States Patent [19]
Dehoff et al.

[11] Patent Number: 5,452,219
[45] Date of Patent: Sep. 19, 1995

[54] METHOD OF MAKING A TOOTH MOLD

[75] Inventors: Barry D. Dehoff, York; Carlton L. Grim, Red Lion; Andrew T. C. Liu, York; Jeffrey E. McGraw, Boiling Springs, all of Pa.

[73] Assignee: Dentsply Research & Development Corp., Milford, Del.

[21] Appl. No.: 219,804

[22] Filed: Mar. 29, 1994

Related U.S. Application Data

[63] Continuation of Ser. No. 536,137, Jun. 11, 1990, abandoned.

[51] Int. Cl.$^6$ .................. G06F 19/00; G05B 19/4099
[52] U.S. Cl. .................. 364/474.05; 364/413.28; 364/474.24; 364/476; 433/223
[58] Field of Search ................ 364/474.05, 474.04, 364/476, 413.28, 474.24; 433/214, 202.1, 206, 212.1, 215, 223, 229, 34, 213, 25, 40, 48; 425/2, DIG. 11; 264/16–20, DIG. 30, 219–227

[56] References Cited

U.S. PATENT DOCUMENTS

| | | | |
|---|---|---|---|
| 3,861,044 | 1/1975 | Swinson, Jr. | 433/214 |
| 4,324,546 | 4/1982 | Heitlinger et al. | 433/25 |
| 4,411,626 | 10/1983 | Becker et al. | 364/474.05 |
| 4,436,684 | 3/1984 | White | 264/16 |
| 4,575,805 | 3/1986 | Moermann et al. | 364/474.05 |
| 4,611,288 | 9/1986 | Duret et al. | 433/213 |
| 4,615,678 | 10/1986 | Moermann et al. | 364/474.05 |
| 4,663,720 | 5/1987 | Duret et al. | 433/214 |
| 4,742,464 | 5/1988 | Duret et al. | 433/214 |
| 4,766,704 | 8/1988 | Brandestini et al. | 51/327 |
| 4,833,617 | 5/1989 | Wang | 364/474.15 |
| 4,837,732 | 6/1989 | Brandestini et al. | 364/413.28 |
| 5,027,281 | 6/1991 | Rekow et al. | 364/474.24 |
| 5,033,014 | 7/1991 | Carver et al. | 364/474.24 |
| 5,092,022 | 3/1992 | Duret | 364/474.05 X |
| 5,224,049 | 6/1993 | Mushabac | 364/413.28 X |

FOREIGN PATENT DOCUMENTS

| | | | |
|---|---|---|---|
| 2197502 | 5/1988 | United Kingdom | 364/474.05 |

Primary Examiner—Joseph Ruggiero
Attorney, Agent, or Firm—Dante James Picciano; Dale R. Loverdheck; Edward J. Hanson, Jr.

[57] ABSTRACT

A method for the making of a tooth mold which includes the steps of scanning the surface of a model of a tooth to obtain data on the three-dimensional surface locations of the model, processing the data in a CAD/-CAM computer, and using the processed data to fabricate a tooth mold. The scanning step involves subjecting a rotating tooth model to radiant energy from a laser beam, receiving and translating reflections of the radiant energy into electronic signals, and digitizing the signals into data of the three-dimensional surface locations of the tooth model. The processing step involves translating the data, editing the data, creating a three-dimensional surface pattern of the tooth model, evaluating the surface pattern by visual analysis and comparison to known geometric values of the tooth model, and creating a tooth path program. Finally, the fabricating step involves using the tooth path program to direct a machine to mill a tooth mold and using the same program to direct a machine to finish-polish the mold.

43 Claims, 1 Drawing Sheet

METHOD OF MAKING A TOOTH MOLD

This is a continuation of application Ser. No. 07/536,137, filed Jun. 11, 1990, abandoned.

BACKGROUND OF THE INVENTION

This invention relates to the fabrication of a mold to make an artificial tooth and more particularly to an operator-assisted, computer-controlled method of fabrication of a tooth mold.

Tooth molds are used in the dental industry for the manufacture of artificial teeth. The making of a tooth mold involves an expensive, time-consuming, and laborious process. In addition, the skills of a master craftsman are required and training a person in the art takes approximately two years.

Briefly, the process of fabricating a working mold or a mold used in the routine manufacture of an artificial tooth involves the following steps. A master die of a tooth is used to form a silicone mold. The silicone mold is used to form a working die made of epoxy resin. The above steps are repeated until a desired number of working dies are produced. Multiple working dies are arranged on a template so that eventually multiple copies of a tooth will be made from a single mold. A silicone mold of the dies on the template is prepared and an epoxy mandrel made from the silicone mold. The mandrel is sprayed with silver to acquire an electrical charge and electroplated with nickel to form a coupon which contains escape ways for excess molding fluid and lands or surfaces between furrows on the coupon. The coupon is then mounted on an aluminum frame, mold guide posts are positioned, and a sprue area for entry of the molding fluid is finished on the aluminum frame. The mounted coupon is refined, hand fitted, and hand polished. After inspection, the mounted coupon is referred to as a master mold which is used to make a working mold. It takes approximately 12 to 14 weeks to make the master mold. In addition, the conversion of the positive image from the master die into the negative image of the master mold involves at least five image reversals.

To prepare a working mold which is used in the routine manufacture of an artificial tooth, an epoxy mandrel is made from a master mold. Thereafter, the process of preparing a working mold is quite similar to the process of preparing a master mold after the epoxy mandrel step, that is spraying, electroplating, and refining. The refining steps include the final hand-applied finish-polish step. This process results in a mold of high-definition of the surface properties of the artificial tooth to be produced. It takes approximately six weeks to make a working mold from a master mold.

In practice, two, three, or more different working molds parts, typically three, namely, a face, a shader, and a back mold, are used in the making of a single artificial tooth. The face mold is used for the fabrication of the labial surface of the tooth; a shader mold is used to make the enamel blend of the tooth surface; and a back mold is used for the construction of the back of the tooth.

As can be appreciated from the above outline of the conventional method of tooth mold manufacture, the process is lengthy, costly, and labor intensive. Computer assistance offers a potential means to overcome some of the disadvantages associated with conventional methods of tooth mold manufacture. The prior art automated systems have not been able to generate the high definitional surface patterns necessary for the production of an artificial tooth.

Examples of patents describing automated methods of the manufacture of dental prosthesis and related subject matter include the following. Swinson in U.S. Pat. No. 3,861,044 teaches a method of fitting a tooth with a dental inlay. The method includes the preparation of a tooth for receiving a dental inlay, producing a photographic signal representation of the prepared tooth, transferring the signal representation to an automatic controlled machine tool, filling the prepared tooth area with wax, producing a photographic signal representation of the tooth filled with wax, transferring the signal representation of the tooth filled with wax to an automatic controlled machine tool operating the automatic machine tool under control of the signal representations to produce a dental inlay, and fitting the prepared tooth with the dental inlay.

Heitlinger et al. in U.S. Pat. No. 4,324,546 disclose an apparatus and method for the manufacture of dentures. The patent describes a method useful in the manufacture of dentures in which a prepared tooth stump is reproduced in a working model and a final denture or a temporary replacement piece is suitably conformed to the working model, including the steps of providing electro-optically produced three-dimensional surface information corresponding to the tooth stump, converting the electro-optically produced information corresponding to the tooth stump by a computer into coordinate control signals, and operating a milling machine automatically from the control signals to reproduce the working model of the stump from a block of material.

White in U.S. Pat. No. 4,436,684 describes methods of making three dimension models and mold cavities of internal body structure comprising subjecting the body to radiant energy to produce radiant energy responses internal to the body, detecting the produced radiant energy responses to obtain representations of substances at locations internal to the body defining structures internal to the body three-dimensionally, generating from the representations of the substances a set of three-dimensional coordinates defining a three-dimensional representation of a selected structure internal to the body, and directing a sculpting tool into a workpiece in accordance with the generated set of three-dimensional coordinates to form a model or mold cavity corresponding to the three-dimensional representation of the selected structure.

Moermann et al. in U.S. Pat. No. 4,575,805 disclose a method and a apparatus for the fabrication of custom-shaped implants. A method is described for facilitating the fabrication of a workpiece to be placed onto a light reflective object having a three-dimensional contour to which the workpiece is to be conformed comprising the steps of noncontact topographic scanning of the contour on the object, directing a pattern of reflected light from the object onto a light sensing means, converting the pattern of light on the light sensing means into a corresponding pattern of electrical data, selecting a set of the electrical data, storing the set of the electrical data, mounting the workpiece onto a machining means which is responsive to electrical data sequentially presented, sequentially presenting the stored set of electrical data to the machining means, and machining the workpiece into a three-dimensional shape in accordance with the stored set of data.

Duret et al. in U.S. Pat. No. 4,611,288 describe a system for taking an impression of a body region for the production of a prosthesis comprising a source of non-traumatic light wave energy for generating waves and directing them at a body region to be examined whereby the waves are reflected from the region, a receiver for the waves reflected from the region for generating analog intensity values representing waves reflected from the region, an analog-numerical converter connected to the receiver for transforming the analog intensity values representing the waves reflected from the region into numerical information representing characteristics of the region, means for receiving the numerical information for three-dimensional analysis of the shape and dimensions of the region from the numerical information and for designing a three-dimensional shape corresponding to a finished prosthesis with a contour adapted to fit the region, and signal processing means connected to the means for receiving the numerical information for transforming an output thereof into machine command signals for direct automatic control of a machine for the direct production of a prosthesis by machining of a workpiece to fit precisely to the region.

Moermann et al. in U.S. Pat. No. 4,615,678 teach a blank from which an implant can be machined by an apparatus of the type disclosed in U.S. Pat. No. 4,575,805. The blank is adapted for use in custom fabrication of an implant for dental restoration and includes first and second joined parts. The first part is made of the raw material of the ultimate implant, whereas the second part can be made of a different material. The second part is shaped to facilitate a positive support of the blank in a milling machine, and is preferably equipped with a code-bearing surface which permits information about the physical properties of the blank to be sensed by the machine.

Duret et al. in U.S. Pat. Nos. 4,663,720 and 4,742,464 disclose a method of making a dental prosthesis in which data representing standard tooth shapes and sizes, relationships between teeth and adjacent and occlusive teeth and characteristics for securing a prosthesis to a prepared site, and machining instructions for shaping a blank to the configuration of a dental prosthesis for direct implantation are stored in a computer memory. After preparing a site in the mouth of a patient to receive a dental prosthesis, the dental surgeon optically projects a grating upon the site in the mouth of the patient and generates an interference pattern representing a holistic impression of the site and its relationship to adjacent structures. The interference pattern is converted into data along x, y, z coordinates in a cartesian coordinate system representing machining of a blank to fit the site and matching data obtained by comparing the impression with the computer standards are used to select a best-fit shape and size. A machine tool is numerically controlled with the x, y, z coordinate data and x, y, z coordinate data from the match made by the computer and representing the shape and size of the prosthesis to totally and three-dimensionally fabricate the prosthesis in the machine tool.

Brandestini et al. in U.S. Pat. No. 4,766,704 describe a method and apparatus for machining a custom-shaped dental restorative part from a blank of dental material in a single operation, and include a workpiece being mounted on a support member which facilitates rotation and axial movement of the workpiece. A separating disk is used for almost the entire machining operation, and an additional tool in the shape of a burr can optionally be provided to shape more elaborate pieces. The disk and burr are supported by a tool holder which is supported for movement parallel to and rotationally about an axis. The disk and burr are powered by a closed loop fluid supply arrangement. A tool velocity sensing scheme is utilized for adaptive feed and to compensate for tool wear. The machining mechanism and associated control circuitry are enclosed in a common cabinet so as to provide a mobile unit suitable for use in a dentist's office.

Brandestini et al. in U.S. Pat. No. 4,837,732 teach a method of facilitating acquisition of data defining the three-dimensional shape of prepared teeth and their immediate vicinity comprising the steps of displaying on a video display a live image from a scan head, manually orienting the scan head relative to the prepared teeth while observing the image of the teeth on the video display, thereafter generating from data produced by the scan head in a selected orientation corresponding depth and contrast images, and thereafter processing the depth image based on the contrast image.

These automated methods may be suitable for the preparation of a single prosthesis but the methods reported are not capable of producing the high definitional qualities needed in a mold that will be repeatedly used in the manufacture of artificial teeth. A high-definition mold is required to produce the labial striations or natural markings on a tooth and multiple molds of high definition are needed to produce the necessary blend of color to give a natural appearance to the molded substance of the artificial tooth. However, only the present invention has a computer operator to interact with the system until an acceptable surface pattern model is attained. The present invention is also the only system to use a tool path program to both direct the milling of a mold and direct the finish-polish of the mold. The computer operator interaction and the tool path program-directed finish-polishing, thus, contribute to the making of the high definition mold of the present invention. The prior art teaches the direct production of dental prosthetic parts using program-directed milling and thus teaches away from indirect (computer operator interaction) methods of mold manufacture of dental prosthetic parts.

It is therefore, the primary object of the present invention to provide a method of making a tooth mold possessing the high definitional qualities needed in the manufacture of artificial teeth.

Another object of the present invention is to provide a method of making a tooth mold in a minimum amount of time.

An additional object of the present invention is to provide a method of making a tooth mold that does not require the skills of an artisan.

A further object of the present invention is to provide a method of making a tooth mold that is not labor intensive and, therefore, is less costly than the conventional process.

These and other objects and advantages of the details of fabricating a dental mold will become apparent after reading the following description of the illustrative embodiment with reference to the attached drawing.

SUMMARY OF THE INVENTION

The above disadvantages of conventional methods of tooth mold manufacture have been overcome by the present invention which basically includes the steps of scanning the surface of a model of a tooth and utilizing data derived from the scan to prepare a negative image of the model of the tooth in a mold suitable for manufacturing an artificial tooth. The method involves the scanning of the tooth model in order to obtain data of the three-dimensional surface of the model, processing the data to create a tool path program, and using the program to control the direct fabrication of a tooth mold which is the negative image of the tooth model.

It should be understood that in addition to teeth other dental prosthetics can be made although tooth production is the preferred form of the invention. By dental model it is meant an actual dental prosthetic part such as an extracted mammalian tooth or a man- or machine-crafted dental prosthetic part or a portion of either an extracted or crafted tooth or other dental part. By dental prosthetic part it is meant to include teeth, crowns, bridges, veneers and other dental restorative units and portions of units. A dental pattern is the negative of the dental model of the dental prosthesis that is to be formed in the dental mold. It will be further understood that the tooth mold will usually be formed as several dental patterns to allow build-up of a tooth from several different layers or materials.

One important feature of the present invention is that the method results in a mold of very high definitional quality. Another important feature of the present invention is that the entire process of producing a mold of a tooth can be reduced to a matter of hours as opposed to the weeks required by the conventional process. A further feature of the present invention is that a tooth mold can be produced which does not require the skills of a master craftsman for its production.

DESCRIPTION OF THE PREFERRED EMBODIMENTS

Figure 1:
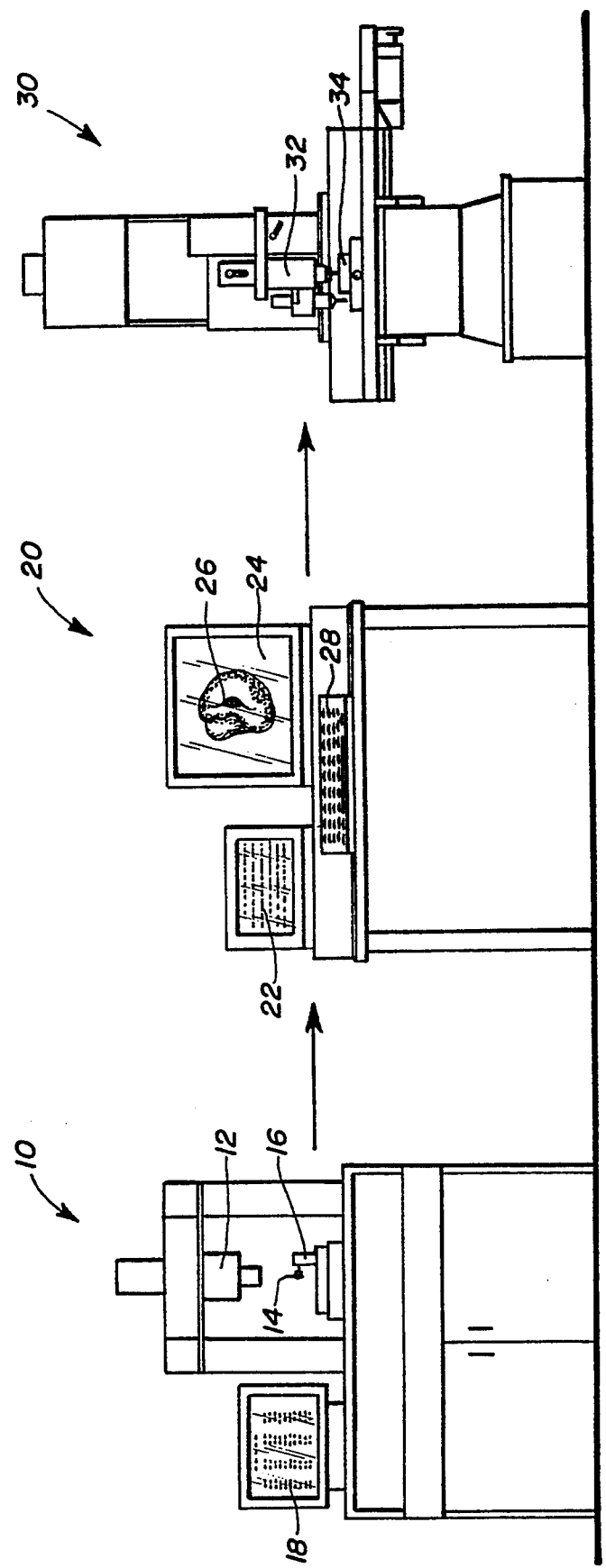
FIG. 1 is a schematic perspective view of an apparatus embodying the present invention including a laser digitizer, a CAD/CAM computer, and a machine tool.

A preferred embodiment of the present invention is shown in FIG. 1. In the schematic, a laser digitizer 10 is interconnected to a CAD/CAM computer 20 which is interconnected to a machine tool 30. It is to be understood that the interconnections between the laser digitizer 10 and the CAD/CAM computer 20 and between the CAD/CAM computer 20 and the machine tool 30 are represented by arrows and not specifically shown. These interconnections may take the form of a cable or the manual transfer of data from machine to machine.

The laser digitizer 10 includes a laser camera 12 which focuses a laser beam on a rotating model of a tooth 14. The laser beam is not shown. The tooth model 14 and the means for rotating the model 16 are shown directly below the laser camera 12. The laser digitizer 10 also has a video display monitor 18. In this first step of making a tooth mold, a tooth model 14 is placed on a revolving support 16 and rotated. The laser camera 12 generates a laser beam and the beam is directed onto the rotating tooth model 14 and reflections from the model are received back by the camera 12. The laser reflections are translated into electrical signals which are converted or digitized into data of the three-dimensional surface locations or contours of the tooth model.

The accuracy of the readings obtained with the laser beam and camera 12 can, if desired, be improved somewhat by the optional step of coating the tooth model 14 with a layer of a reflective, non-glare substance. Such a layer provides substantially uniform contrast at various locations across the tooth model 14.

The digitized data is translated into machine readable language by a translator (not shown) and is transferred to the CAD/CAM computer 20 for processing. The computer 20 comprises two video display monitors, 22 and 24, and the hardware necessary for the programs to function. The CAD or computer-assisted design part of the computer is used to design process the data in order to produce the three-dimensional surface pattern or map of the tooth model. The first step of the processing is to subject the digitized data from the laser scan to a computer-controlled software editing program. This computer-controlled software program filters, smooths, and otherwise normalizes the digitized data.

The edited digitized data is used to create a three-dimensional surface pattern of the tooth model. The three-dimensional surface pattern 26 can be displayed on one video display monitor 24 while the values from the edited digitized data can be displayed on the other monitor 22. At this point, a computer operator interacts with the system before the data is processed further. The operator examines the surface pattern for the high definitional qualities, such as the size and shape of the tooth and labial striations, needed for the dental mold. If an acceptable degree of definition as determined by visual analysis and comparison to known geometric values, e.g., length, width, thickness, for the tooth model is not present, the operator can add, via keyboard 28 control, supplemental data not previously used (data generated in the original laser digitization of the tooth model but not used in the creation of the previous three-dimensional surface pattern of the tooth model) or repeat the digitizing at a higher degree of laser beam resolution (perform again laser beam analysis of the tooth model but using a greater laser beam resolving power to generate new data). In either event, a new three-dimensional surface pattern is created. The computer operator interaction process can be repeated until an acceptable surface pattern model is generated.

If the three-dimensional surface pattern is definitionally acceptable, the CAM or computer-assisted manufacture part of the computer is used to process the data in order to produce a tool path program for the fabrication of the dental mold. The tool path program is used to direct and control a machine tool 30. The machine will preferably be of multi-axes. The program will direct a milling cutter 32 or cutters in the milling of a tooth mold 34 from a suitable substrate, for example, steel, nickel, aluminum, ceramic, plastic or any machinable material. Steel is the preferred substrate. After the mold has been cut, the tool path program is preferably used to direct and control the application of the finish-polish to the mold. The finish-polish step improves the surface finish and results in a mold suitable for the manufacture of artificial teeth. A final hand-applied finish-polish step is optional. The mold or coupon formed by this process may be of the type that is mounted for operation in a mold frame and operated in standard fashion; in other instances, the entire mold may be formed or multiple cavity molds may be made.

It is to be understood that the present invention is not limited to the use of a laser beam for the scanning of the tooth model. Any source of imaging energy, such as an electron beam or sonic waves, that would give data readings of sufficient resolution to produce a mold of sufficient definition would be acceptable. In addition, digitized data acquired from other sources, e.g., binocular photography or optical interferometry, may be used. The tooth model itself can be selected from any dental sources having the definitional qualities needed to be transferred to the dental mold. Examples of acceptable models may include carvings, extracted teeth, artificial teeth, master dies, or even master or working tooth molds. The models may be made of any material suitable of showing the necessary definition. Examples of suitable materials include, but are not limited to, waxes, ceramics, glass, porcelain, plastic and metals. The metal models include elemental metals, alloys, metal/ nonmetal mixtures, as well as nonmetal models coated with metals.

In a preferred embodiment, the scanning of the tooth model is performed on a rotating three-dimensional model which is situated on a revolving support. The laser scanning of a three-dimensional rotating model allows for the immediate interconnection or integration of individual scan points. Such immediate interconnection of data points increases the rate of data processing and thereby decreases the time needed to prepare the tool path program.

As previously mentioned, the fabrication method of a tooth mold for the manufacture of an artificial tooth requires a high degree of definition as compared to a method for the preparation of other prostheses. A high-definition mold is required to produce the labial striations or markings on a tooth and multiple molds are needed to produce a blend of color capable of producing a natural appearance in the artificial tooth.

Blending refers to the use of a mold to produce a body base of given proportions and the use of additional mold parts to produce the outer coating of given proportions. This combination of layers can be varied to create an assortment of optical appearances for the artificial tooth. Also, the color of the substance from which an artificial tooth is to be molded may be varied to create another assortment of optical appearances or mechanical properties for the artificial tooth. It follows that the color of the layers in the blending process may be varied to create a myriad of optical appearance or mechanical properties for the artificial tooth or other prostheses.

In a preferred embodiment of the present invention, a computer operator interacts with the system at a point prior to the production of a tool path program. Just as the computer operator can examine the surface pattern of the tooth model, the operator can add supplemental data from storage (data generated in the original laser digitization of the tooth model but not used in the creation of the previous three-dimensional surface pattern of the tooth model) or repeat the scanning and digitizing at a greater level of resolution. In either event, a new three-dimensional surface pattern will be created which can be examined or analyzed for the required values or visual appearances. A skilled operator is necessary and each production is anticipated to require manipulation; the operator need not, however, be specifically skilled in making tooth molds.

Having generally described the invention, a more complete understanding can be obtained with reference to the specific Example, which is included for purposes of illustration only. It should be understood that the invention is not limited to the specific details of the Example.

EXAMPLE

An aluminum bronze (alloy) master die was coated with a layer of a glarefree substance for making the face mold part for an upper central tooth. The coated master die was placed on a revolving support in a Surveyor Model 2000, 3D Laser Digitizing System available from Laser Design, Inc., Minneapolis, Minn. The glarefree substance on the master die was then re-applied to eliminate any imperfections in the coating. The master die was read at a scanning speed of 100 points per second with each point spaced 0.002 of an inch from the next. A stepover scanning distance of 0.005 of an inch was used. The laser beam had a diameter of 0.00275 of an inch and the system accuracy was plus or minus 0.00075 of an inch. Actual scanning time for the die was four hours. The digitized information or scanned data was collected on a memory disk, 65 megabyte hard disk, and transferred to a floppy disk.

The floppy disk was inserted into an IGES (International Graphics Exchange Standard) translator which translated the digitized information or scanned data from the laser into machine readable language. The IGES translator is available from Laser Design, Inc., Minneapolis, Minn. The translated data was collected on a floppy disk and inserted into a Saber 5000 CAD/CAM System, available from Gerber Systems Technology, Inc., South Windsor, Conn. The translated data was edited within the CAD/CAM system and a three dimensional model displayed on a video display monitor. The values from the edited digitized data were displayed on a second monitor. The computer operator examined the surface pattern for size and shape of the tooth and the labial striations for the high definitional qualities needed for the fabrication of the dental mold and determined that the needed qualities were not attained with the original surface pattern model. The operator then tested various combinations of supplemental data (data generated in the original laser digitization of the tooth model but not used in the creation of the previous three-dimensional surface pattern of the tooth model) to generate additional surface pattern models. The process was repeated until a surface pattern having the size and shape of the tooth model and the size and the shape of the labial striations of the tooth model was attained. The parting line for the face mold part or point of contact with another mold part was provided by the computer operator at the time of evaluating the surface pattern of the tooth model. Once an acceptable surface pattern was generated, the Sabre 5000 CAD/CAM System software was used to generate a tool path program for the making of the dental mold. The data in the form of the numerical coordinates of the tool path program were collected on a memory disk and down loaded or transferred to a floppy disk.

The floppy disk was down loaded into the hard disk drive of a BostoMatic Model 312-1S Vertical CNC Bed Type Precision Milling, Drilling, Boring and Contouring Machine, available from Boston Digital Corporation, Milford, Mass. The tool path program was used to direct and control the machine in the fabrication of the tooth mold. The feed rate averaged 6 inches per minute (range 4.5–10 inches per minute), at 30,000 rpm, for four consecutive passes with mills of decreasing size. A quarter inch end mill (Bassett) was followed by an eighth inch end mill (Bassett), followed by a sixteenth inch ball end mill (Bassett), followed by a thirty-second inch ball end mill (TSC Carbide). The tool path accuracy was 0.0002 inch and the stepover range was 0.001–0.005 inch. The machine has four axis capability but only three axes were used in the making of the mold. The mold was cut into a block of 420 free machining stainless steel. The resultant mold was tested for surface finish qualities by subjective visual evaluation with the trained eye at 7X magnification comparing stone impressions from the mold with the aluminum bronze master die. It was determined that the machined mold contained approximately 95% of the surface detail and finish of the master die. The mold created was a coupon that was mounted into a standard aluminum mold frame for proof molding.

The remaining 5% surface detail and finish should be supplied by finish-polishing. It is presently contemplated that the finish-polishing will be accomplished with the finish tool path program using a finish-polishing tool. The finish-polishing tool comprises a hard wood polishing stick and is used with a diamond paste; the finish-polishing step is used to get as close as possible to the complete and acceptable surface detail and finish. It is very probable that a final hand polishing step will be carried out using a dental handpiece (power tool), brush (synthetic bristles), and jewelers' rouge.

For making the back mold part, the digitized information from the scan of the amuminum bronze master die was processed up to readiness to be down loaded into the hard disk drive of the milling machine. For making the shader mold part, a soft Babbitt master shader die (not coated with a glarefree substance) was placed on a revolving support and processed in the same manner as the aluminum bronze master die described above. The data was processed in the same manner as for the aluminum bronze master die information up to readiness to be down loaded into the hard disk drive of the milling machine. The data was smoothed on the screen during editing to assure the fit of the shader mold part into the face mold part.

It will be apparent to those skilled in the art that various modifications and changes may be made in the practice and use of the method without departing from the scope of the present invention as set forth in the following claims.

What is claimed is:

1. A method of repeatedly molding high definition artificial dental teeth each having a molded coating, comprising:
   scanning a model of a dental tooth, and
   milling to make at least three mold parts each said part being milled with a first mill by executing a first pass along a first tool path to remove material to form multiple cavities in a first metal block to make a multiple cavity mold part adapted to form multiple dental prosthetic teeth, said milling being directed by a milling program which uses edited data, said edited data being obtained by editing reflection data using a design program, said reflection data being representative of the surface of said tooth model, said edited data being representative of the surface of said dental artificial teeth, said edited data being adapted by said milling program to direct said milling along said tool path and
   repeatedly molding in said mold high definition artificial dental teeth each having a molded coating.

2. The method of claim 1 wherein each said cavity is the negative of a portion of said model of a dental tooth to be molded in the mold; and the program is produced by the steps of imaging the surface contours of the dental model and producing data readings in response to the imaging of the surface contours of the model.

3. The method of claim 1 further comprising directing polishing of at least one of said mold parts by a finish tool path program.

4. The method of claim 3 wherein said polishing comprises finish-polishing using a finish tool path and a finish-polish tool.

5. The method of claim 4 wherein said tool is used with a paste.

6. The method of claim 5 wherein said paste is diamond paste.

7. The method of claim 4 wherein said tool comprises wood.

8. The method of claim 1 wherein said milling further comprises making a second pass along said tool path with a second mill having a second mill end, said second mill end being smaller in size than said first mill end.

9. The method of claim 8 wherein said milling further comprises a making third pass along said tool path with a third mill having a third mill end, said third mill end being smaller in size than said second mill end.

10. The method of claim 8 wherein said milling further comprises making a third pass with a third mill having a third mill end, said third mill end being smaller in size than said second mill end.

11. The method of claim 10 wherein said milling further comprises making a fourth pass with a fourth mill having a fourth mill end, said fourth mill end being smaller in size than said third mill end.

12. The mold of claim 1 wherein said mold part is a face mold part.

13. The method of claim 1 wherein said mold part is a shader mold part.

14. The method of claim 1 wherein a point of contact with a second part is provided using a surface pattern of said mold.

15. The method of claim 12 further comprising
   milling with said first mill by executing a first pass along a second tool path to remove material to form multiple cavities in a second block to make a multiple cavity second mold part.

16. The method of claim 15 wherein said mold part is a back mold part.

17. The method of claim 16 further comprising milling with a second mill by making a second pass along said second tool path to remove material from said second block.

18. A method of making artificial dental teeth each having a molded coating and high definition labial striations comprising the steps of:
   providing a dental tooth model,
   scanning said tooth model,
   receiving reflections from said tooth model,
   translating said reflections into electronic signals,
   converting said electronic signals into reflection data,
   editing said reflection data to add high definition labial striations using a design program to provide edited data and
   fabricating a metal tooth mold part, said fabricating step comprising using said edited data to direct machine milling of said tooth mold part, said milling comprising making a first pass with a first mill and making a second pass with a second mill, said first mill having a first mill end, said second mill having a second mill end, said second mill end being smaller in size than said first mill end, and repeatedly molding in said mold part, high definition artificial teeth each having a molded coating and high definition labial striations.

19. The method of claim 18 wherein said scanning comprises directing a laser beam onto said dental tooth model.

20. The method of claim 18 wherein said scanning step further comprises rotating said dental tooth model during said subjecting and receiving steps.

21. The method of claim 18 wherein said tooth model is a three-dimensional replica of a tooth, said model comprising metal.

22. The method of claim 18 wherein said dental tooth model is a natural tooth.

23. The method of claim 18 wherein said dental tooth model is a wax model of a tooth.

24. The method of claim 18 wherein said processing step comprises,
creating an edited three-dimensional surface pattern of said tooth model from said edited data, evaluating said surface pattern of said dental tooth model, and creating a tool path program from said edited data.

25. The method of claim 24 wherein said evaluating step further comprises visual analysis of said surface pattern of said dental tooth model and comparison to known geometric values for said tooth model.

26. The method of claim 18 wherein said fabricating step further comprises using said tool path program to finish-polish said dental tooth mold part.

27. A method of molding a artificial dental teeth each having a molded coating and labial striations comprising the steps of:
scanning a three-dimensional replica of a tooth having three-dimensional surface locations while rotating said replica, receiving reflections from said replica while rotating said replica,
translating said reflections into electronic signals, and
digitizing said electronic signals into reflection data editing said reflection data to add high definition labial striations to provide edited data in a computer using a CAD/CAM program, and
creating a tool path program using said edited data, and fabricating said tooth mold, said fabricating step comprising, using said tool path program to direct machine milling of a first, second and third metal artificial dental teeth mold parts,
said milling of said first metal mold part from a first metal part comprising making a first pass with a first mill and making a second pass with a second mill to mill said first metal part, said first mill having a first mill end, said second mill having a second mill end, said second mill end being smaller in size than said first mill end,
said milling of said second metal mold part from a second metal part comprising making a first pass with said first mill and making a second pass with said second mill to mill said second mold part,
said milling of said third metal mold part from a third metal part comprising making a first pass with said first mill and making a second pass with said second mill to mill said third mold part.

28. The method of claim 27 wherein said replica of a tooth comprises metal.

29. The method of claim 27 wherein said replica of a tooth comprise a glarefree coating.

30. The method of claim 27 wherein said tooth mold comprises a metal substrate.

31. The method of claim 27 wherein said fabricating step further comprises using said tool path program to direct machine finishing-polishing said mold part.

32. The method of claim 27 wherein said milling further comprises making a third pass with a third mill having a third mill end, said third mill end being smaller in size than said second mill end.

33. The method of claim 32 wherein said milling further comprises making a fourth pass with a fourth mill having a fourth mill end, said fourth mill end being smaller in size than said third mill end.

34. A method of molding artificial dental teeth each having a molded coating and labial striations, comprising:
milling multiple patterns of artificial teeth in first and second portions of mold making material to make first and second mold parts, said milling being directed by a milling program which uses edited data, said edited data being provided by editing reflection data using a design program, said reflection data being representative of the surface of a tooth model, said edited data being representative of the surface of said artificial tooth, said edited data being adapted by said milling program to direct said milling of said first and second mold parts,
said milling of said first mold part comprising executing a first pass with a first mill and executing a second pass with a second mill, said first mill having a first mill end, said second mill having a second mill end, said second mill end being smaller in size than said first mill end;
said milling of said second mold part comprising executing a first pass with a third mill and executing a second pass with a fourth mill, said third mill having a third mill end, said fourth mill having a fourth mill end, said third mill end being smaller in size than said fourth mill end;
repeatedly molding in said mold high definition artificial dental teeth each having a molded coating and labial striations.

35. The method of preparing a dental mold of claim 34 wherein said mold making material is readily machinable and polishable.

36. The method of preparing a dental mold of claim 34 wherein said mold making material is steel, nickel, aluminum, ceramic or plastic.

37. A method of molding artificial teeth each having a molded coating and high definition labial striations, comprising:
milling multiple patterns of artificial teeth in a mold making material to make first, second and third mold parts, said milling being directed by a milling program which uses edited data, said edited data being provided by editing reflection data using a design program, said reflection data being representative of the surface of a tooth model, said edited data being representative of the surface of said artificial tooth, said edited data being adapted by said milling program to direct said milling, said milling of each of said parts comprising executing a first pass with a first mill and executing a second pass with a second mill, said first mill having a first mill end, said second mill having a second mill end, said second mill end being smaller in size than said first mill end,
repeatedly manufacturing high definition artificial teeth having labial striations in said mold.

38. The method of claim 34 wherein said milling further comprises making a third pass with a third mill having a third mill end, said third mill end being smaller in size than said second mill end.

39. The method of claim 38 wherein said milling further comprises making a fourth pass with a fourth mill having a fourth mill end, said fourth mill end being smaller in size than said third mill end.

40. The method of preparing a dental mold of claim 37 wherein said mold making material is readily machinable and polishable.

41. The method of preparing a dental mold of claim 37 wherein said mold making material is steel, nickel, aluminum, ceramic or plastic.

42. The method of claim 37 wherein said milling further comprises making a third pass with a third mill having a third mill end, said third mill end being smaller in size than said second mill end.

43. The method of claim 32 wherein said milling further comprises making a fourth pass with a fourth mill having a fourth mill end, said fourth mill end being smaller in size than said third mill end.

* * * * *